United States Patent [19]

Love et al.

[11] Patent Number: 5,531,785
[45] Date of Patent: Jul. 2, 1996

[54] PROSTHETIC HEART VALVE HOLDER

[75] Inventors: Jack W. Love, Santa Barbara; Charles S. Love, Newbury Park; Philip J. Hudak, Burbank; Robert W. Suggitt, Newbury Park, all of Calif.

[73] Assignee: Autogenics, Inc., Newbury Park, Calif.

[21] Appl. No.: 239,345

[22] Filed: May 6, 1994

[51] Int. Cl.$^6$ ............................... A61F 2/24; A61B 17/00
[52] U.S. Cl. ........................ 623/2; 623/900; 606/1; 606/99
[58] Field of Search ................ 623/2, 900; 606/1, 606/99, 108, 113

[56] References Cited

U.S. PATENT DOCUMENTS

| | | |
|---|---|---|
| 3,548,418 | 12/1970 | Angell et al. . |
| 3,587,115 | 6/1971 | Shiley . |
| 4,065,816 | 1/1978 | Sawyer . |
| 4,084,268 | 4/1978 | Ionescu et al. . |
| 4,443,895 | 4/1984 | Lane . |
| 4,470,157 | 9/1984 | Love . |
| 4,512,471 | 4/1985 | Kaster et al. . |
| 4,679,556 | 7/1987 | Lubock et al. . |
| 4,801,015 | 1/1989 | Lubock et al. . |
| 4,838,288 | 6/1989 | Wright et al. . |
| 4,865,600 | 9/1989 | Carpentier et al. ............... 623/2 |
| 4,881,562 | 11/1989 | Wright et al. . |
| 5,011,481 | 4/1991 | Myers et al. ....................... 606/1 |
| 5,041,130 | 8/1991 | Cosgrove et al. ................. 623/2 |
| 5,163,955 | 11/1992 | Love et al. ......................... 623/2 |
| 5,314,435 | 5/1994 | Green et al. ..................... 606/153 |
| 5,360,014 | 11/1994 | Sauter et al. .................... 128/774 |

FOREIGN PATENT DOCUMENTS

| | | | |
|---|---|---|---|
| 103546 | 3/1984 | European Pat. Off. ............. 623/2 |
| 207339 | 12/1969 | U.S.S.R. ............................ 623/2 |
| 1008937 | 7/1984 | U.S.S.R. ............................ 623/2 |
| 2213730 | 8/1989 | United Kingdom ............... 606/1 |
| WO9203990 | 3/1992 | WIPO . |

OTHER PUBLICATIONS

"A Suture Holder and Separator Attachment to the Starr–Edwards Prosthetic Valve Holders", Grismer et al.; Surgery, Gynecology & Obstetrics, Mar. 1965, pp. 583–584.
Love et al., "Rapid Intraoperative Fabrication of An Autogeneous Tissue Heart Valve: A New Technique".
Reul et al., "In Vitro Testing of Bioprostheses", vol. XXXIV Trans Am Soc Artif Intern Organs, 1988, pp. 1033–1039.
Black et al., "A construction Technique for Minimising Valve Leaflet Fatigue Failure in Pericardial Valves", Proceedings XI Annual Meeting ESAO, Alpbach–Innsbruck, Austria, Sep. 1984, vol. 2.

Primary Examiner—David Isabella
Assistant Examiner—Laura Fossum
Attorney, Agent, or Firm—Knobbe, Martens, Olson & Bear

[57] ABSTRACT

The present invention provides a prosthetic heart valve holder specifically configured to hold a prosthetic heart valve comprised of a stent. The heart valve holder assembly has three main components: a handle, a valve capture loop assembly and a valve retainer. The prosthetic heart valve is secured to the valve retainer by a loop of suture as the surgeon sutures or attaches the valve to the annulus of the heart. Thus, the valve holder assembly facilitates attachment of the prosthetic valve to the annulus so that the procedure may be performed in a time and labor efficient manner.

16 Claims, 7 Drawing Sheets

PROSTHETIC HEART VALVE HOLDER

FIELD OF THE INVENTION

This invention relates to prosthetic heart valve holders and a method of using prosthetic heart valve holders and is particularly directed to holders and methods for using holders which are configured to be quickly attachable to a prosthetic heart valve and serve to hold the valve in place while the surgeon sutures or attaches the prosthetic heart valve to the annulus of a patient's heart.

BACKGROUND OF THE INVENTION

Heart valve replacement is required when a patient's heart valve becomes diseased or damaged. The heart valve replacement procedure requires that the diseased or damaged heart valve be removed from the patient and replaced with some type of artificial or prosthetic valve. In order to implant the valve, the prosthetic valve must be held in place while the surgeon sutures or attaches the prosthetic heart valve to the annulus of the heart.

A conventional method of attaching a prosthetic valve to the annulus of the heart requires that the surgeon or technician hold the valve in place during the attachment procedure. Due to the limited amount of space in the heart, it is difficult to properly position and hold the valve at the site of the annulus.

In addition, in order to properly align the replacement valve with the annulus and maintain alignment until the valve is securely attached, the procedure normally requires a team of at least two highly skilled people. Thus, one person holds the replacement valve in place while the other person sutures or attaches the replacement valve to the annulus.

Several disadvantages are associated with the abovementioned conventional valve replacement procedure. First, in order to both hold the prosthetic valve in place and securely attach it to the annulus, several people are required to perform the procedure. Thus, the procedure is time and labor inefficient. Next, due to the limited amount of space in the heart, it is difficult to properly align the replacement valve with the annulus and maintain the valve-annulus alignment. Further, due to the number of people required and the limited space available during the procedure, it is difficult for the surgeon or technician to properly view and visually inspect the area where the procedure is being performed. This, in turn, can lead to improper valve-annulus attachment, with increased risk to the patient.

SUMMARY OF THE INVENTION

The present invention provides a novel heart valve holder to securely hold the replacement prosthetic heart valve at the site of the annulus during a heart-valve replacement procedure. The preferred embodiment of this invention includes three main elements: a handle, a valve bell-jar or retainer cup, and a valve capture loop assembly. The valve capture loop assembly, located near the distal end of the handle, is comprised of a plastic base piece, a spring and a monofilament suture. The valve retainer cup is made of plastic and attaches to the externally threaded section at the distal end of the handle. The valve retainer cup is generally cylindrical in shape and is used to cup or hold the outflow portion of the replacement valve.

In use, a replacement heart valve is housed within the valve retainer cup so that the inflow portion of the replacement prosthetic heart valve is seated against the distal end of the valve retainer cup. The prosthetic heart valve is temporarily secured in this position by the valve capture loop assembly which advantageously includes a biased monofilament suture in the form of a loop which is secured around the base of the heart valve.

A significant advantage of this invention over conventional valve holders is the speed by which the replacement valve attaches to the heart valve holder. Due to the simple yet effective design of the valve holder, a completed replacement valve can be securely attached to the valve holder within seconds. In order to accomplish this, the surgeon simply positions the replacement valve inside the retainer cup and loops the monofilament suture over the base of the replacement valve. Thus, the entire assembly attachment procedure is accomplished in a time-efficient manner. This feature is of special importance for autologous tissue valves constructed in accordance with the teachings of U.S. Pat. Nos. 4,470,157 and 5,163,955 and the following copending U.S. patent applications: Ser. No. 07/930,231, filed Aug. 22, 1992, entitled *Rapid Assembly Concentric Mating Stent, Tissue Heart Valve with Enhanced Clamping and Tissue Alignment;* Ser. No. 07/925,589, filed Aug. 3, 1992, entitled *Rapid Assembly Concentric Mating Stent, Tissue Heart Valve with Enhanced Clamping and Tissue Alignment;* Ser. No. 07/925,380, filed Aug. 3, 1992, entitled *Rapid Assembly Concentric Mating Stent, Tissue Heart Valve with Enhanced Clamping and Tissue Alignment;* Ser. No. 07/925,376, filed Aug. 3, 1992, entitled *Rapid Assembly Concentric Mating Stent, Tissue Heart Valve with Enhanced Clamping and Tissue Alignment;* Ser. No. 08/169,620, filed Dec. 17, 1993, entitled *Tissue Cutting Die;* Ser. No. 08/169,618, filed Dec. 17, 1993, entitled *Heart Valve Measurement Tool;* and, Ser. No. 08/169,336, filed Dec. 17, 1993, entitled *Stents for Autologous Tissue Heart Valve.* These issued patents and copending patent applications are assigned to Autogenics, assignee of the present invention, and disclose methods and apparatus for constructing prosthetic heart valves in the operating room during the open heart procedure.

A significant feature of the present invention is that once the replacement valve is securely attached to the valve holder, the surgeon or technician can easily manipulate the valve holder assembly so that the inflow portion or base of the replacement valve is properly aligned with the annulus of the heart. The surgeon sutures the base of the replacement valve to the annulus and then cuts one leg of the monofilament suture of the valve holder assembly. The valve holder, along with the monofilament suture, is then detached from the replacement valve by being easily pulled away from the permanently attached prosthetic heart valve.

Another important advantage of this invention is that the suture, which is part of the valve capture loop assembly, occupies only a very small area of the inflow portion of the prosthetic heart valve. As a result, the base of the prosthetic heart valve being sutured into the heart annulus remains relatively unobstructed to the surgeons performing the open heart surgery.

Additional advantages of the present invention are the physical characteristics and function of the monofilament suture. The suture is comprised of a lubricous material which allows the suture to be readily and easily removed from the permanently attached prosthetic heart valve. Further, compared to multifilament materials, the monofilament suture causes less friction against the tissue and leaves no material remnants within the valve as it is pulled away from the permanently attached prosthetic heart valve.

Yet another advantage of the heart valve holder of the present invention is the function of the retainer cup. The retainer cup not only holds the assembled prosthetic valve during the attachment procedure, but also provides a protective cover for the outer stent of the prosthetic valve during shipment. By surrounding the outer stent, the retainer cup functions as a protective shield, thereby protecting the outer stent from shipping damage, such as tears, scratches and other deformities.

In addition, the retainer cup is very advantageous for installing tissue prosthetic heart valves by inhibiting moisture in the leaflets of the assembled valve from evaporating. The hot lights used in the operating room tend to dry out the tissue forming the assembled tissue valve. This adverse condition is inhibited, however, by the present invention which houses the replacement valve inside the retainer cup to provide a high humidity space for the valve. Thus, the retainer cup provides the valve tissue with protection from evaporative loss throughout the attachment procedure.

These and additional features and advantages of the present invention will become apparent from the detailed description which follows, considered together with the drawings and claims.

DETAILED DESCRIPTION OF THE INVENTION

Figure 1:
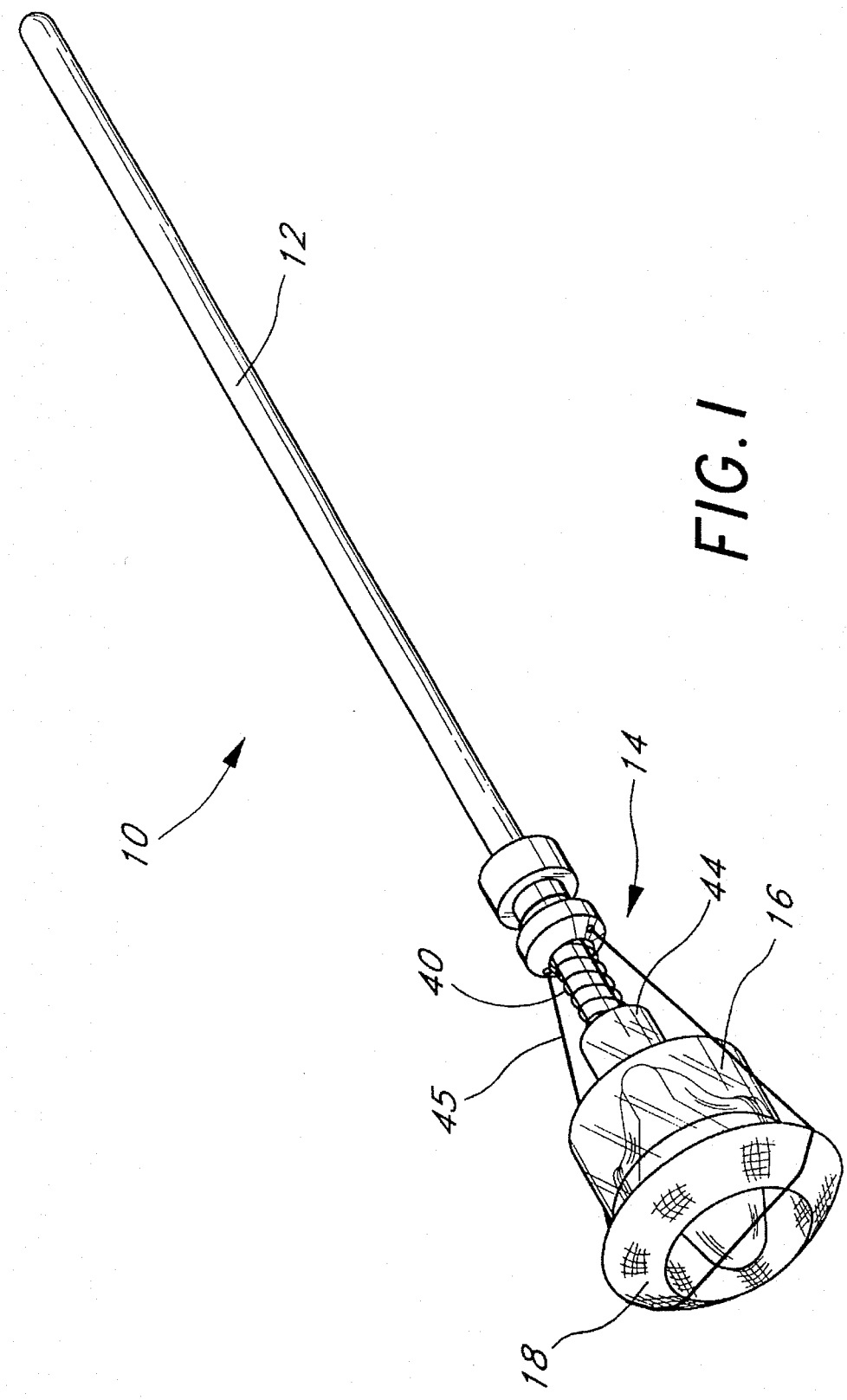
FIG. 1 is a perspective view of the valve holder assembly of the present invention.

FIG. 1 illustrates a perspective view of the valve holder 10 attached to a prosthetic heart valve 18 just prior to surgical implantation of the valve 18 into the patient. Valve holder 10 includes a handle 12, a valve capture loop assembly 14 including spring 40, and a valve bell-jar or retainer cup 16. The valve holder 10 is specifically configured to hold a prosthetic heart valve 18 while the surgeon or technician sutures or attaches the prosthetic heart valve 18 to the annulus of the heart.

Figure 2:
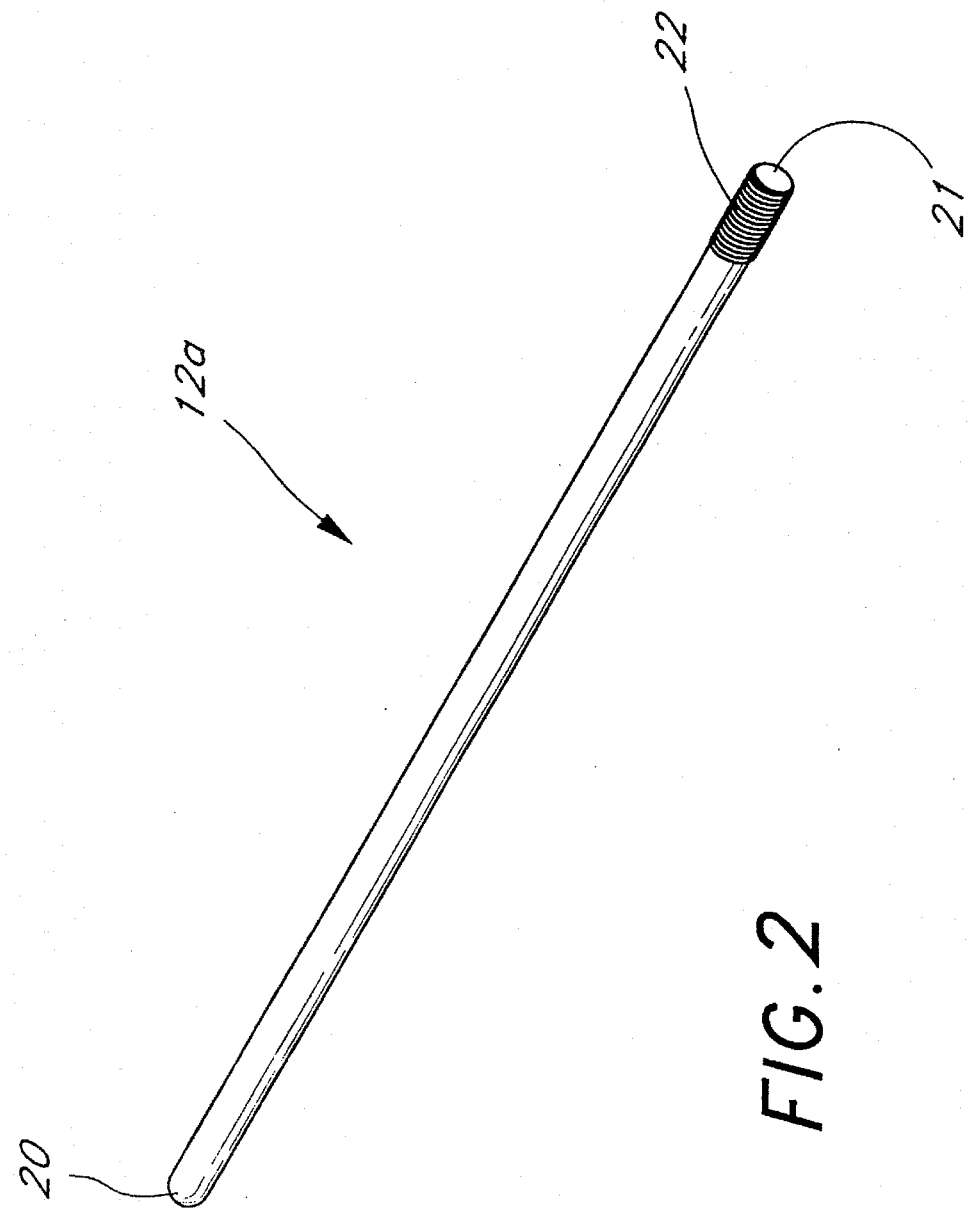
FIG. 2 is a perspective view of one embodiment of the handle of the present invention.
Figure 3:
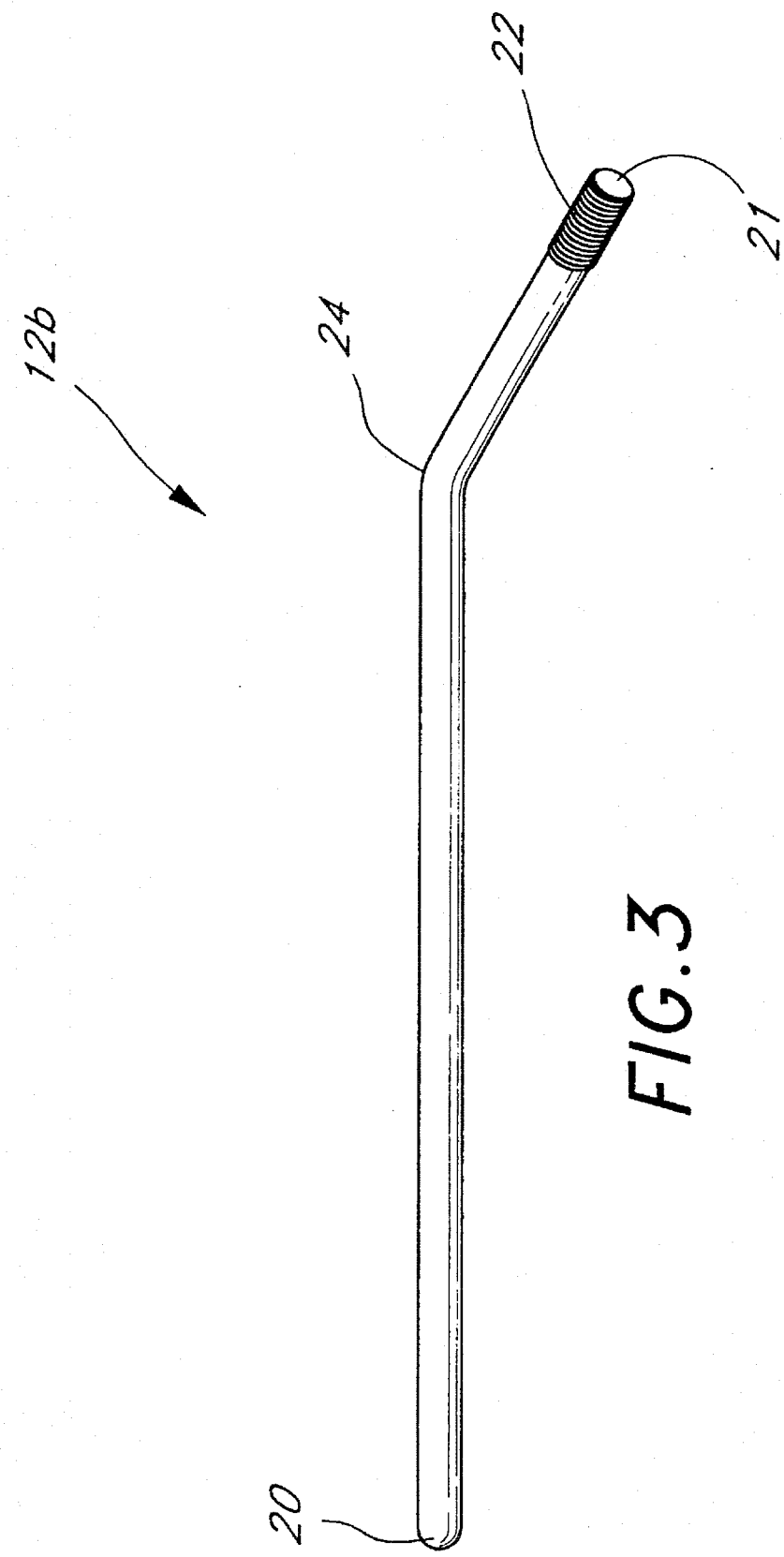
FIG. 3 is a perspective view of a second embodiment of the handle of FIG. 2 having a bent distal portion.
Figure 4:
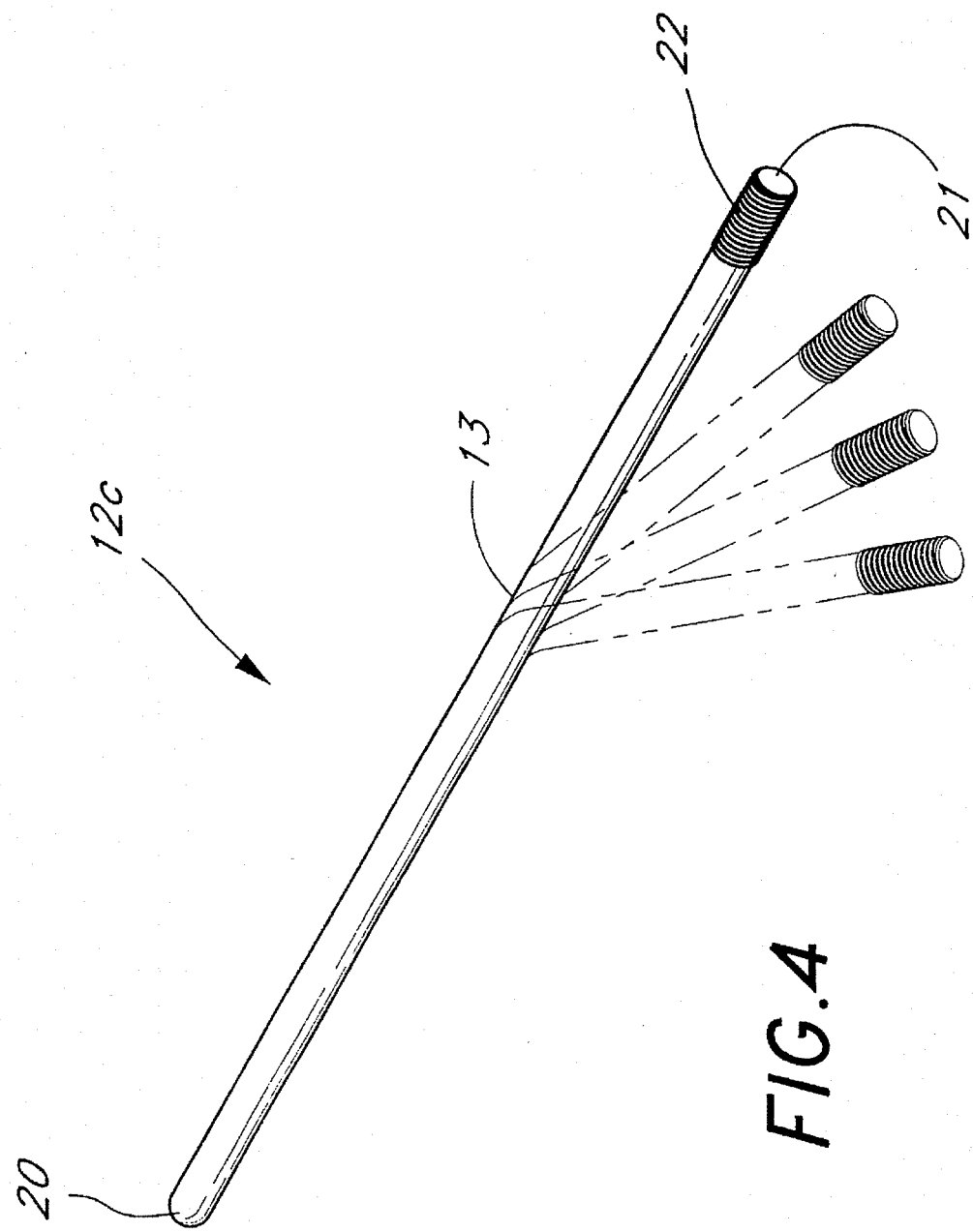
FIG. 4 is a perspective view of a third embodiment of the handle of FIG. 2 having a malleable middle section.

Three embodiments 12a, 12b and 12c of the handle 12 of the valve holder 10 are illustrated in FIGS. 2–4. As shown in FIG. 2, the handle 12a of the valve holder assembly 10 is generally cylindrical or rod shaped with a rounded proximal end 20 and a distal end 21 having external threads 22. The valve holder 16 attaches to the threads 22 at the distal end 21 of the handle 12. Each handle 12b and 12c shown in FIGS. 3 and 4 also attaches to the valve holder 16 via threads 22 located at the distal end 21.

Referring to FIG. 3, handle 12b has a bend 24 located near its distal end 21 which may assist in maneuvering and positioning the replacement valve 18. As described below, the valve holder 10 advantageously allows the user to simultaneously hold and position the prosthetic valve 18 at the site of the annulus with minimal obstruction to the user of the device. Thus, the area to be viewed is relatively unobstructed and there is adequate space for the surgeon or technician to suture the prosthetic valve 18 to the annulus.

In the first and second embodiments of the handle 12 just described, the handle shape as delivered to and used by the surgeon remains substantially the same.

In another embodiment, shown in FIG. 4, the handle 12c of the present invention includes a malleable middle section 13. The malleable middle section 13 is constructed so that the surgeon or user of the device may bend or manipulate the handle 12c into the desired configuration, including but not limited to the bend 24 in the handle 12b of FIG. 3. Thus, the design and material of the malleable middle section 13 of the handle 12c permits the user of the device to reconfigure the handle 12c into an alternate conformation if so desired and provides the user of the device with an infinite number of handle 12c configurations to more easily and precisely position the replacement valve 18 over the annulus of the heart.

In the preferred embodiment shown, the handle 12a or 12b or 12c is attached by external threads 22 at its distal end 21. It will be apparent, however, that other ways of attachment may be used. One example of same is a quick-disconnect mechanism (not shown) to provide a positive or frictional lock. In this alternate embodiment, the surface of the distal end 21 of the handle 12 creates a positive or frictional lock with the handle attachment portion 44 of the retainer cup 16 (shown in FIG. 7). For this embodiment, the outer surface of the distal end 21 of the handle 12 creates a frictional force against the attachment portion 44 of the retainer cup 16, thereby securing the handle 12 onto the retainer cup 16. In an alternate embodiment, the attachment portion 44 of the retainer cup 16 is comprised of a spring and an L-shaped slot (not shown). The distal end 21 of the handle 12 of the present invention includes a notch or tab (not shown), whereby the tab slides into the L-shaped slot of the retainer cup 16 and, with the tension created by the spring, securely attaches the handle 12 onto the retainer cup 16. It should be noted, however, that the attachment mechanism of the present invention is not limited to those described above, but may also include other comparable attachment mechanisms as is well known by those skilled in the art.

The handle 12 of the present invention may be made of metal or other materials that can be cleaned or sterilized in an autoclave, as is well known by those skilled in the art. In another embodiment, the handle 12 is made of an inexpensive plastic and, thus be disposable.

Figure 6:
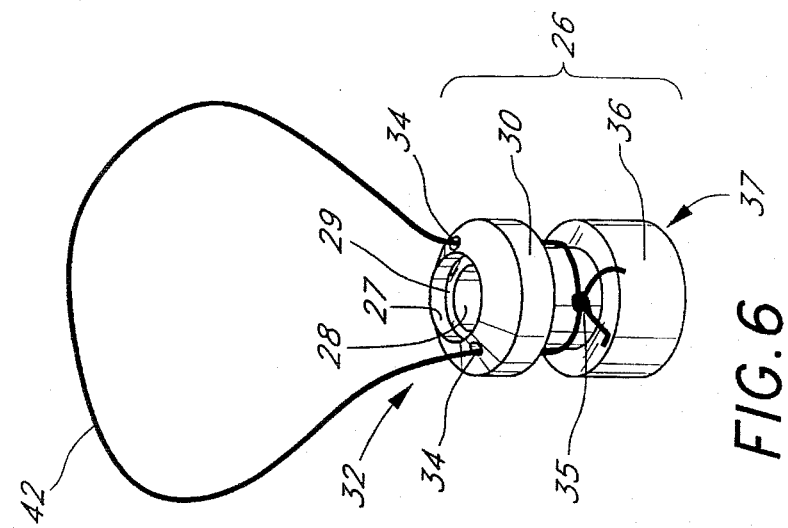
FIG. 6 is a detailed perspective view of the monofilament suture tied to the base piece.
Figure 5:
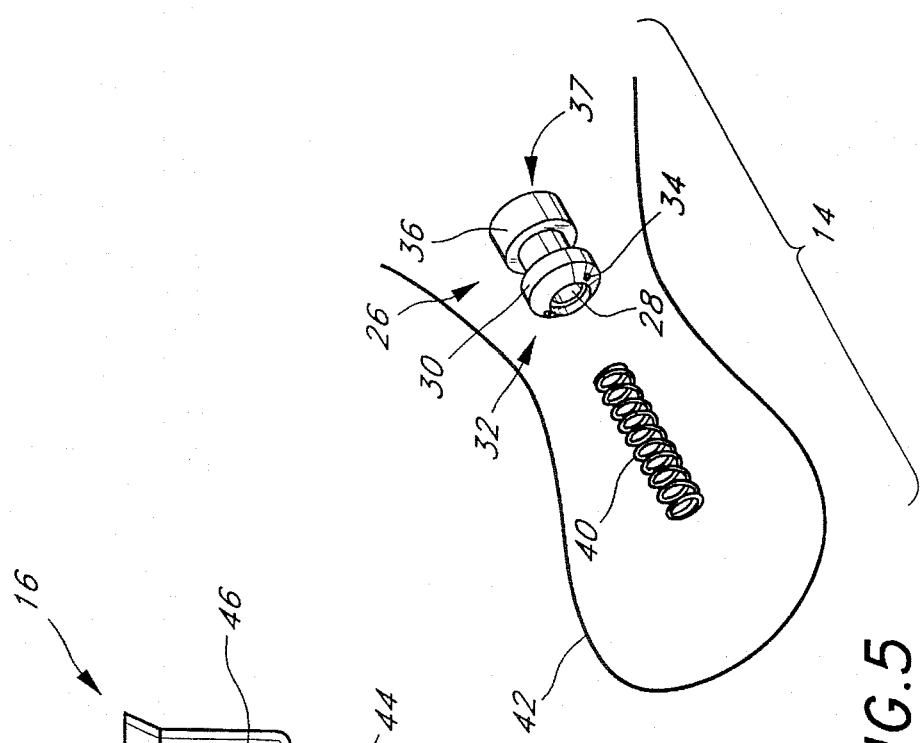
FIG. 5 is an exploded perspective view of the valve capture assembly of FIG. 1.

The valve capture loop assembly 14 is located near the distal end 21 of the handle 12 and is advantageously comprised of just three components, as best shown in FIGS. 5 and 6. The first component of the valve capture loop assembly 14 is the base piece 26. The base piece 26 is made of plastic and is generally cylindrical in shape. A hole or hollowed-out portion 28 is located along the axis of the base piece 26. The opening 27 at the distal end 32 of base piece 26 is larger than hole 28, thereby forming a shoulder 29 best seen in FIG. 6. The diameter of the hole 28 is slightly greater than the diameter of the cylindrical or rod-shaped handle 12 so that the handle 12 can be inserted through the hole 28 of the base piece 26 and the base piece 26 is free to slide along the handle 12. A first ring 30 is formed near the distal end 32 of the base piece 26. This formed ring 30 has two through-holes 34 spaced 180° apart. The through-holes 34 are used as the attachment points for the third component of the valve capture assembly 14. The base piece 26 also has a second ring 36 formed at its proximal end 37.

Still referring to FIGS. 5 and 6, the second and third components of the valve capture assembly 14 are the spring 40 and a length of monofilament suture 42, respectively. The spring 40 is of sufficient diameter so as to allow it to slide over the distal end 21 of the handle 12. In addition, one end of the spring 40 fits within the opening 27 in abutment with the shoulder 29 at the distal end 32 of the base piece 26. Once assembled onto the handle 12, the other end of the spring 40 seats against the attachment portion 44 of the retainer cup 16, as shown in FIG. 1.

The length of monofilament suture 42 of FIGS. 5 and 6 is attached through the holes 34 of the first ring 30 of the base piece 26. One end of the suture 42 is threaded through one through-hole 34, while the other end of the suture 42 is threaded through the opposite through-hole 34. The two ends of the suture 42 are then tied together, thereby forming a knot 35. The knot is located between the first ring 30 and second ring 36 of the base piece 26. The location of the knot 35 between the first 30 and second 36 rings prevents the suture 42 from becoming detached from the base piece 26.

Figure 9:
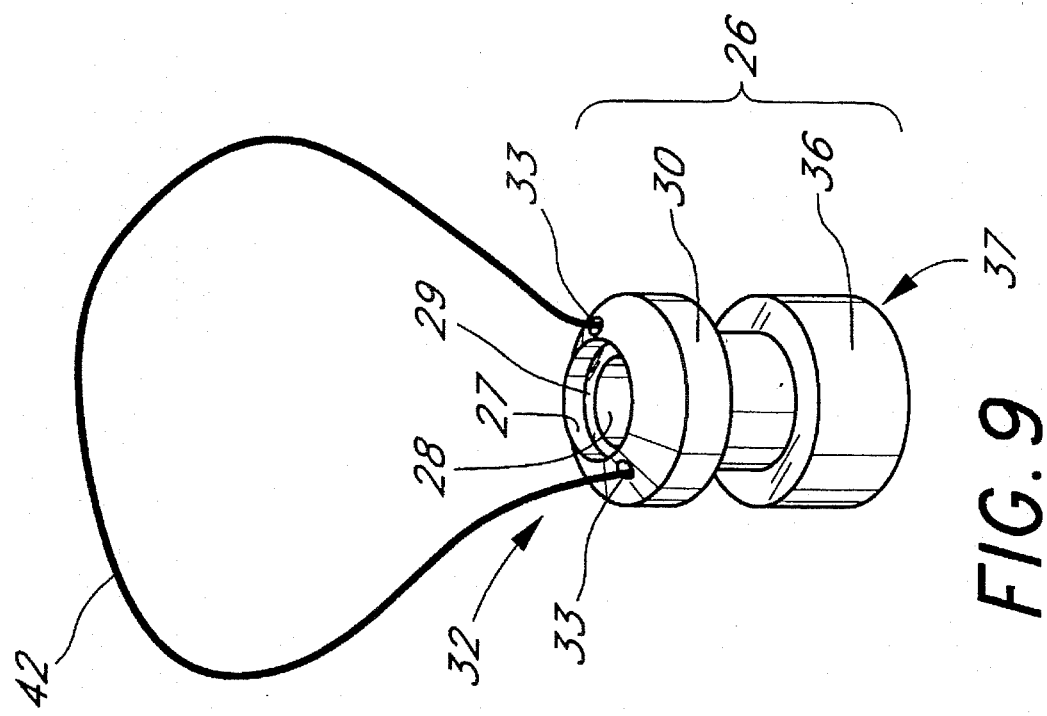
FIG. 9 is a perspective view of an alternate means of attaching the monofilament suture to the base piece.

Another method of attaching the monofilament suture 42 to the base piece 26 includes molding the suture 42 into the base piece 26. In still another embodiment as illustrated in FIG. 9, the two ends of the monofilament suture 42 can be cemented with epoxy at 33 to the base piece 26. Other methods of securing the monofilament suture 42 to the base piece 26 are also acceptable provided that the monofilament suture 42 remains securely attached to the base piece 26.

While only a single loop of suture 42 is shown in this preferred embodiment, two or more loops located through additional openings may also be used to retain the valve 18 within the retainer cup 16.

In order to allow the suture 42 to be readily and easily removed form the permanently attached prosthetic heart valve 18, the length of suture 42 is advantageously comprised of a lubricous, monofilament material. The smooth, slippery outer surface of the suture 42 reduces the amount of friction against the tissues. In addition, the suture 42 leaves no material remnants within the valve 18 as the suture 42 is pulled away from the permanently attached prosthetic heart valve 18. Thus, the physical characteristics and function of the monofilament suture 42 of the present invention prevents the suture 42 from tearing or contaminating the tissues of the valve 18.

Figure 7:
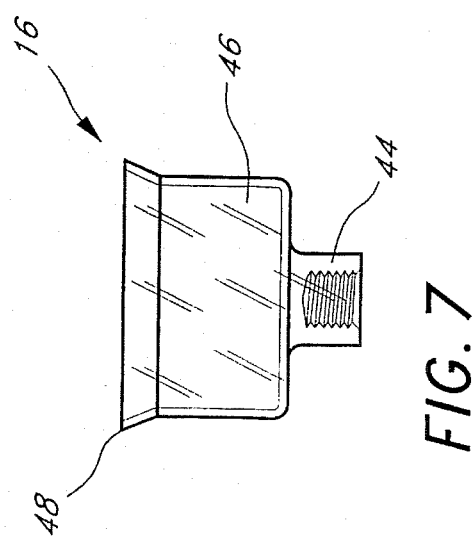
FIG. 7 is a perspective view of the valve holder of FIG. 1.

The final component of the valve holder 10 assembly is the valve retainer cup 16. As shown in FIG. 7, the retainer cup 16 has two sections. The first section is the internally threaded attachment portion 44 which screws onto the external threads 22 at the distal end 21 of the handle 12. The second section 46 of the retainer cup 16 is the cup portion which is used to cup or temporarily hold the replacement valve 18. This second section 46 has a cylindrical or bell-jar shape and is specifically configured to hold the outflow portion of the replacement valve 18, as shown in FIG. 1. Referring back to FIG. 7, the distal end 48 of the second section 46 tapers outwardly, thereby forming a larger diameter portion, onto which the inflow portion or base of the replacement valve 18 nests. The retainer cup 16 is typically made of a transparent plastic, thereby allowing the user of the device to visually inspect the assembly to ensure that the replacement valve 18 is properly seated in the retainer cup 16, as shown in FIG. 1.

In addition to functioning as a temporary holder for the replacement valve 18, the retainer cup 16 of the present invention also functions as a protective cover for the outer stent. During shipment, there is the potential for the outer stent of the prosthetic heart valve 18 to deform or tear. However, by seating the outer stent inside the retainer cup 16, the outer stent is protected from most shipping damage. Thus, the retainer cup 16 provides a protective shield or cover for the outer stent of the prosthetic valve 18 during shipment.

In addition, the retainer cup 16 also inhibits moisture from evaporating from the valve 18 leaflets. The operating room environment typically includes hot lights which can cause moisture to evaporate from the valve 18 tissue. This detrimental condition, however, is avoided by housing the replacement valve 18 inside the retainer cup 16 of the present invention. Thus, the retainer cup 16 provides a high humidity area for the valve 18 and, subsequently, protects the valve 18 tissues from evaporative losses throughout the attachment procedure.

Figure 8:
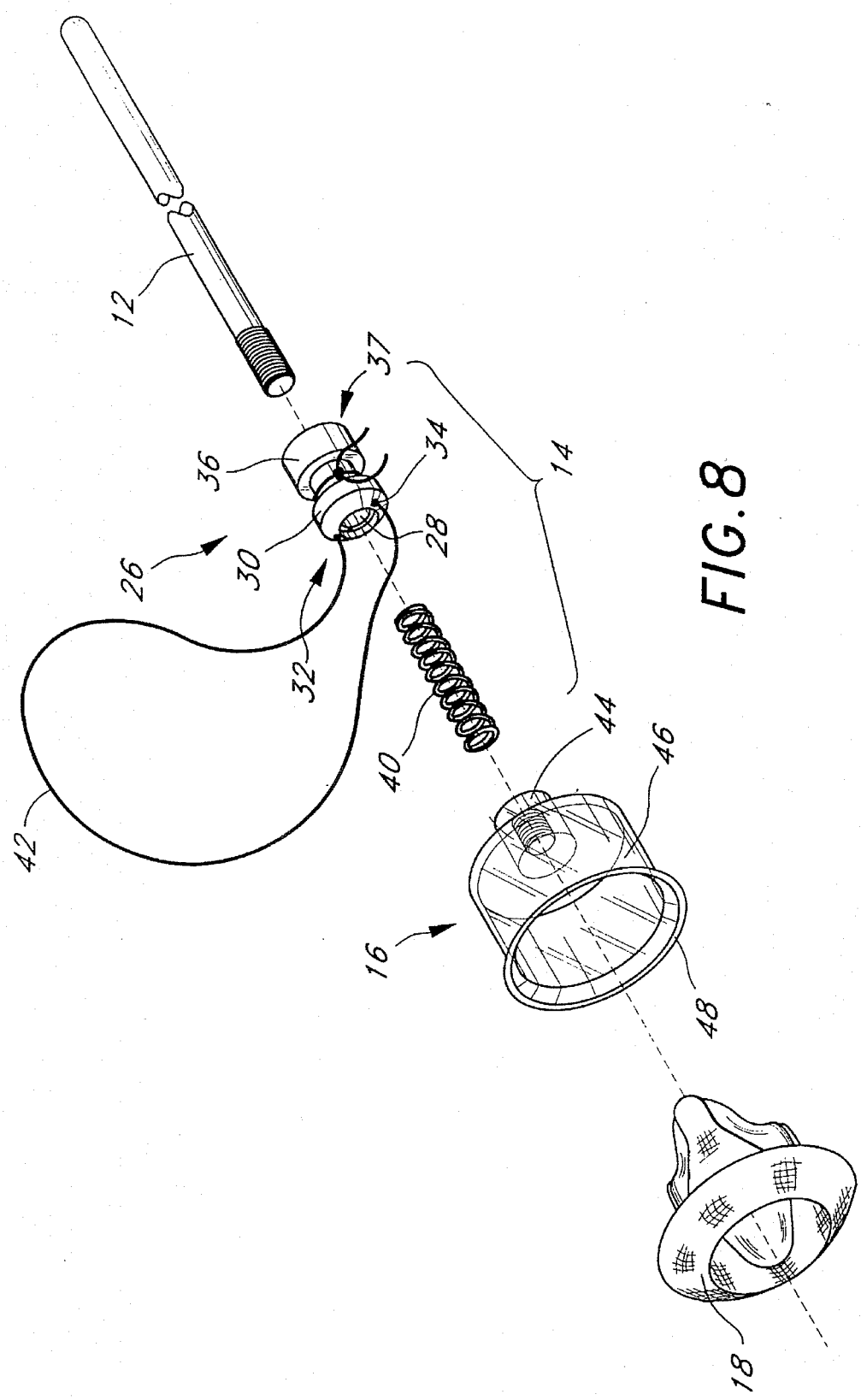
FIG. 8 is an exploded perspective view of the valve holder assembly of FIG. 1.

The method of using the valve holder 10 assembly of the present invention is as follows. Referring to FIGS. 1, 6 and 8, a replacement valve 18 is housed within the second section 46 of the retainer cup 16. The replacement valve 18 is properly positioned in the retainer cup 16 when the top portion of the base of the replacement valve 18 is seated against the distal end 48 of the retainer cup 16. Next, the base piece 26 of the valve capture loop assembly 14 is biased against the spring 40 toward the retainer cup 16. Once the spring 40 is completely compressed, the monofilament suture 42 has sufficient slack so as to be looped over the replacement valve 18. Finally, the base piece 26 is released so that the spring 40 returns to its extended position and thereby secures the replacement valve 18 to the retainer cup 16 of the valve holder 10 via the biased looped suture 42.

Once the replacement valve 18 is secured within the retainer cup 16 by the suture 42, the surgeon or technician can easily manipulate the valve holder 10 so that the base of the replacement valve 18 is properly aligned with the annulus of the heart. After suturing the base of the replacement valve 18 to the annulus of the heart, the surgeon cuts the monofilament suture 42 of the valve holder 10 assembly.

A significant advantage of the valve holder 10 assembly is that, as shown in FIG. 1, the valve 18 is attached to the valve holder 10 by a single monofilament suture 42. Accordingly, the base of the prosthetic heart valve 18 is almost totally unobstructed to the physician sewing the valve 18 into the patient's heart.

An important feature of the present invention is that the valve holder 10 is quickly and safely removed from the installed replacement heart valve 18 by merely cutting one leg of the monofilament suture 42 anywhere along the section of suture 42 extending from the second section 46 of the retainer cup 16 to the first ring 30 of the base piece 26. Once the suture 42 has been cut, the valve holder 10 is easily pulled away from the replacement valve 18 and the cut monofilament suture 42 readily detaches from the patient. In addition, and most important, the suture 42 remains attached to the valve holder 10 due to the knot 35 tied between the first ring 30 and second ring 36 of the base piece 26. Thus, the knot 35 at this location serves the dual function of providing secure attachment of the monofilament suture 42 to the valve holder 10 and also positively ensures that all of the monofilament suture 42 is locked to this valve holder 10 and is pulled out of the patient after the monofilament suture 42 is cut.

Another important advantage of the valve holder 10 of the present invention is the speed by which the surgeon can attach the replacement valve 18 to the valve holder 10. Due to the simple construction and effective design of the valve holder 10, a surgeon can securely attach the completed replacement valve 18 to the valve holder 10 in a minimal amount of time, typically within seconds. As described above, the surgeon simply positions the replacement valve 18 inside the retainer cup 16 and loops the monofilament suture 42 over the base of the replacement valve 18. Thus, the entire attachment procedure is accomplished in a time-efficient manner.

Obviously, numerous variations and modifications can be made without departing form the spirit of the present invention. Therefore, it should be clearly understood that the forms of the present invention described above and shown in the figures of the accompanying drawings are illustrative only and are not intended to limit the scope of the present invention.

What is claimed is:

1. A valve holder for holding a prosthetic heart valve having an inflow portion and an outflow portion so that the valve is (i) accurately positioned at an annulus of a patient's heart remaining after removal of a patient's diseased heart valve, (ii) temporarily held in place without substantially obstructing the valve while a surgeon or technician attaches the valve within the patient's heart while said valve is temporarily held in place by the holder, and (iii) quickly and easily removed after the prosthetic heart valve has been permanently attached at said annulus, said valve holder comprising:

a cup shaped retainer defining an inner cavity, said retainer having an open receiving end configured to accept said outflow portion of said prosthetic heart valve within said cavity;

a valve capture loop assembly comprising a base, a loop of suture attached to said base, and a spring for biasing said base and its attached loop of suture; and a rod member inserted through said base and said spring and attached to said cup shaped retainer opposite its open receiving end, said rod member serving (i) as a handle for the surgeon or technician attaching said valve, (ii) for slidably mounting said base member, and (iii) for retaining said spring between said cup shaped retainer and said base of said valve capture loop assembly;

said holder configured to capture said prosthetic heart valve to the holder with said loop of suture so that (i) only a very minimal area of said valve is obstructed when said valve is held in place within said patient's heart, and (ii) configured such that said prosthetic heart valve is very easily removed from said holder after its attachment within said heart by simply cutting said loop of suture to completely release said prosthetic heart valve from said holder.

2. A valve holder assembly having a length of monofilament line for securing and precisely positioning a prosthetic heart valve having an outflow portion and a base during the implantation of said valve into the annulus of the heart of a patient, comprising:

a handle having a distal and a proximal end, said distal end having external threads;

a valve capture assembly including a cylindrical base piece having a first ring located at a distal end of said base piece and including a plurality of holes, a second ring located proximally from said first ring on said base piece, and a hollowed-out portion extending through said base piece along its longitudinal axis, said valve capture assembly further including a length of monofilament line attached to said first ring where said length of monofilament line is configured to be looped over said base of said valve, said valve capture assembly further including a spring engaging said distal end of said base piece, said handle inserted into said hollowed-out portion of said cylindrical base piece; and a valve holder having a cup portion defining an inner cavity, said holder, specifically configured to hold said outflow portion of said valve within said valve and an internally threaded attachment portion for threadable engagement with said distal end of said handle, said cup portion connected to said handle and said attachment portion registering against a distal end of said valve capture assembly spring so that said spring applies tension to said monofilament line.

3. The valve holder assembly of claim 2, wherein said handle is straight.

4. The valve holder assembly of claim 2, wherein said handle has a bend located near its distal end.

5. The valve holder assembly of claim 2, wherein said handle has a malleable middle section.

6. The valve holder assembly of claim 2, wherein said handle is made of an autoclavable material.

7. The valve holder assembly of claim 2, wherein said handle is disposable.

8. The valve holder assembly of claim 2, wherein said valve holder is made of a semi-transparent plastic.

9. The valve holder assembly of claim 2, wherein said monofilament line is made of a lubricous material.

10. The valve holder assembly of claim 2, wherein said valve retainer is a protective cover which prevents moisture from evaporating from prosthetic heart valve leaflets.

11. The valve holder assembly of claim 2, wherein said valve retainer is a protective shield for an outer stent of the prosthetic heart valve.

12. The valve holder assembly of claim 2, wherein said monofilament line has a first end and a second end and is secured to said base piece by tying together the ends of said monofilament line, thereby creating a knot which resides between said first ring and said second ring of said base piece.

13. The valve holder assembly of claim 2, wherein said monofilament line is secured to said base piece by molding said monofilament line into said base piece.

14. The valve holder assembly of claim 2, wherein said monofilament line is secured to said base piece by epoxy.

15. A valve holder assembly for precisely positioning a prosthetic heart valve having a base and an outflow portion during implantation of said valve into the heart of a patient, comprising:

a cup defining an inner cavity configured to retain the outflow portion of said prosthetic heart valve;

a valve capture assembly having a base piece, a segment of line attached to said base piece, and a spring having a first and a second end, said line configured to hold said base of said valve in said cup during implantation of said valve, said first end of said spring engaging said base piece and said second end of said spring engaging said cup, whereby said spring biases said base piece away from said cup for supplying tension to said line during the implantation of said valve; and a handle having a threaded distal end, said handle threadably engageable with said cup.

16. A valve holder assembly for precisely positioning a prosthetic heart valve, having an outflow portion and a base, during the implantation of said valve into an annulus of the heart of a patient, comprising:

a handle having a distal and a proximal end, a valve capture assembly including a cylindrical base piece having a first ring located at the distal end of said base piece and including a plurality of holes, a second ring located proximally from said first ring on said base piece, and a hollowed-out portion extending through said base piece along its longitudinal axis, said valve capture assembly further including a length of monofilament line attached to said first ring where said length of monofilament line is configured to be looped over the base of said valve, said valve capture assembly further including a spring, said handle inserted into said hollowed-out portion of said cylindrical base piece; and a valve holder having a cup portion defining an inner cavity, said holder specifically configured to hold the outflow portion of said valve within said cavity and an attachment portion for attachable engagement with said distal end of said handle, said cup portion connected to said handle and said attachment portion registering against said spring.

* * * * *